US009443161B2

(12) United States Patent
Guo (10) Patent No.: US 9,443,161 B2
(45) Date of Patent: Sep. 13, 2016

(54) METHODS AND SYSTEMS FOR PERFORMING SEGMENTATION AND REGISTRATION OF IMAGES USING NEUTROSOPHIC SIMILARITY SCORES

(71) Applicant: Dimensions and Shapes, LLC, Tampa, FL (US)

(72) Inventor: Yanhui Guo, Miami, FL (US)

(73) Assignee: Dimensions and Shapes, LLC, Tampa, FL (US)

(*) Notice: Subject to any disclaimer, the term of this patent is extended or adjusted under 35 U.S.C. 154(b) by 0 days.

(21) Appl. No.: 14/518,976

(22) Filed: Oct. 20, 2014

(65) Prior Publication Data

US 2015/0242697 A1 Aug. 27, 2015

Related U.S. Application Data (60) Provisional application No. 61/943,622, filed on Feb. 24, 2014.

(51) Int. Cl.
*G06K 9/00* (2006.01)
*G06K 9/34* (2006.01)
(Continued)

(52) U.S. Cl.
CPC .............. *G06K 9/34* (2013.01); *G06K 9/6267* (2013.01); *G06T 3/0068* (2013.01); *G06T 3/0093* (2013.01); *G06T 7/0012* (2013.01); *G06T 7/0014* (2013.01); *G06T 7/0038* (2013.01); *G06T 7/0042* (2013.01); *G06T 7/0081* (2013.01); *G06T 19/006* (2013.01); *G06F 19/321* (2013.01); *G06T 2207/10072* (2013.01); *G06T 2207/10088* (2013.01); *G06T 2207/10132* (2013.01); *G06T 2207/20141* (2013.01); *G06T 2207/20144* (2013.01); *G06T 2207/30004* (2013.01); *G06T 2207/30068* (2013.01);
(Continued)

(58) Field of Classification Search
USPC ........................................................ 382/128
See application file for complete search history.

(56) References Cited

U.S. PATENT DOCUMENTS

| | | | |
|---|---|---|---|
| 7,478,091 B2* | 1/2009 | Mojsilovic | ........ G06F 17/30256 |
| 2006/0274928 A1* | 12/2006 | Collins | .................... A61B 6/00 |
| | | | 382/132 |

OTHER PUBLICATIONS

Buddingh et al., Intraoperative assessment of biliary anatomy for prevention of bile duct injury: a review of current and future patient safety interventions, Surg Endosc (2011) 25:24490132461, 13 pages.

(Continued)

*Primary Examiner* — Yon Couso
(74) *Attorney, Agent, or Firm* — Foley & Lardner LLP (57) ABSTRACT

A medical imaging system includes an imaging device configured to scan a region of interest to acquire at least one of a first image including a first plurality of pixels and a second image including a second plurality of pixels, a processing unit configured to receive the first and second images, calculate respective first neutrosophic similarity scores for each of the first plurality of pixels of the first image, calculate respective second neutrosophic similarity scores for each of the second plurality of pixels of the second image, perform a template matching algorithm based on differences between the respective first and second neutrosophic similarity scores for each of the first and second plurality, respectively, to determine one or more registration parameters, and register the first and second images using the one or more registration parameters, and a display output configured to allow the registered first and second images to be displayed.

12 Claims, 5 Drawing Sheets

(51) Int. Cl.
    *G06K 9/62*     (2006.01)
    *G06T 3/00*     (2006.01)
    *G06T 7/00*     (2006.01)
    *G06T 19/00*     (2011.01)
    *G06F 19/00*     (2011.01)

(52) U.S. Cl.
    CPC ................ *G06T2207/30096* (2013.01); *G06T 2207/30196* (2013.01)

(56) References Cited

OTHER PUBLICATIONS

Cannon et al., Real Time 3-Dimensional Ultrasound for Guiding Surgical Tasks, Computer Aided Surgery (2002), 8 pages.

Gao et al., Prostate Segmentation by Sparse Representation Based Classification, Med Image Comput Comput Assist Interv. 2012 ; 15(Pt 3): 451013458, 10 pages.

Keereweer et al., "Optical Image-guided Surgery—Where Do We Stand?", Molecular Imaging and Biology (2011) 13:199-207, 9 pages.

Liu et al., Fully Automatic 3D Segmentation of Iceball for Image-Guided Cryoablation, Conf Proc IEEE Eng Med Biol Soc. 2012 ; 2012: 2327-2330, 10 pages.

Nakano et al., Fusion of MRI and sonography image for breast cancer evaluation using real-time virtual sonography with magnetic navigation: first experience, Jpn J Clin Oncol 2009;39(9)552013559, 8 pages.

\* cited by examiner

METHODS AND SYSTEMS FOR PERFORMING SEGMENTATION AND REGISTRATION OF IMAGES USING NEUTROSOPHIC SIMILARITY SCORES

CROSS REFERENCE TO RELATED PATENT APPLICATIONS

This application is related to U.S. Application No. 61/943,622, titled "Methods and Systems for Performing Segmentation and Registration of Images using Neutrosophic Similarity Scores," filed Feb. 24, 2014; which is incorporated herein by reference in its entirety.

BACKGROUND

Real-time visualization is an actively growing area in different scientific areas. The medical field is not an exception, and tumors, vessels and organs are visualized more accurately as technology improves, and recently the potential to perform a real-time visualization has not only been possible but the addition of this technology have shown improved results in interventional procedures. Buddingh K T, et al. "Intraoperative assessment of biliary anatomy for prevention of bile duct injury: a review of current and future patient safety interventions." *Surg Endosc*. 2011; 25:2449-61; Keereweer S, et al. "Optical image-guided surgery—where do we stand?" Mol Imaging Biol. 2011; 13:199-207; and Cannon J W, Stoll J A, et al. "Real-time three-dimensional ultrasound for guiding surgical tasks." *Comput Aided Surg*. 2003; 8:82-90. Furthermore, during a real-time visualization and evaluation, prior analysis of a particular area or volume of interest could be imported, to assist in the current evaluation of the image. Nakano S, et al. "Fusion of MRI and sonography image for breast cancer evaluation using real-time virtual sonography with magnetic navigation: first experience." *Jpn J Clin Oncol*. 2009; 39:552-9. Conventional techniques involve co-registration and segmentations algorithms.

Co-registration techniques display prior images, with their associated analysis, and import them as the real-time image, approximating its position and orientation based on software calculation. This position is approximated using different methods such as marking the patient (tattooing), placing the patient on the table in a very similar position as in the prior exam, or using real-time imaging (e.g., ultrasound co-registration) to approximate the area where the data should be imported. Regardless of the co-registration technique, this image is not the "real-time" image and any changes is position, manipulation of surrounding tissues or simple changes in tissue volumes (secondary to the pliability of the tissues) render this static, prior image inaccurate. Segmentation techniques are similarly powerful and allow the user to visualize a particular organ or area of interest in a user friendly fashion. These techniques recognize particular tissues based on their image intensities and can show them in a three-dimensional manner and some of them in an automatic fashion. Gao Y, et al. "Prostate segmentation by sparse representation based classification." *Med Image Comput Comput Assist Interv*. 2012; 15:451-8; Liu X, et al. "Fully automatic 3D segmentation of iceball for image-guided cryoablation." *Conf Proc IEEE Eng Med Biol Soc*. 2012; 2012:2327-30. The drawback of these techniques is the limited ability to import prior analysis, preventing useful prior evaluations to be considered during this real-time assessment.

SUMMARY

One embodiment relates to a medical imaging system. The medical imaging system includes an imaging device configured to scan a region of interest to acquire at least one of a first image including a first plurality of pixels and a second image including a second plurality of pixels, a processing unit, and a display output configured to allow the registered first and second images to be displayed. The processing unit is configured to receive the first image from a first scan, calculate respective first neutrosophic similarity scores for each of the first plurality of pixels of the first image, segment the region of interest from a background of the first image using a region growing algorithm based on the respective first neutrosophic similarity scores for each of the first plurality of pixels, detect the region of interest in a second scan based on a distance from a skin to the region of interest to localize the region of interest, receive the second image from the second scan, calculate respective second neutrosophic similarity scores for each of the second plurality of pixels of the second image, perform a template matching algorithm based on differences between the respective first and second neutrosophic similarity scores for each of the first and second plurality of pixels of the first and second images, respectively, to determine one or more registration parameters, and register the first and second images using the one or more registration parameters. The respective first neutrosophic similarity scores for each of the first plurality of pixels provide a set of parameters, one parameter being the distance from the skin to the region of interest.

Another embodiment relates to a method for use with a medical imaging system and for registering a plurality of images containing an object. The method for use with a medical imaging system and for registering a plurality of images containing an object including receiving a first image including a first plurality of pixels from a first scan at a processor, calculating, by the processor, respective first neutrosophic similarity scores for each of the first plurality of pixels of the first image, segmenting, by the processor, an object from a background of the first image using a region growing algorithm based on the respective first neutrosophic similarity scores for each of the first plurality of pixels, receiving a margin adjustment related to the object segmented from the background of the first image at the processor, detecting, by the processor, the region of interest in a second scan based on a distance from skin to the region of interest to localize the region of interest, receiving a second image including a second plurality of pixels from the second scan at the processor, calculating, by the processor, respective second neutrosophic similarity scores for each of the second plurality of pixels of the second image, performing, by the processor, a template matching algorithm based on differences between the respective first and second neutrosophic similarity scores for each of the first and second plurality of pixels of the first and second images, respectively, to determine one or more registration parameters, registering, by the processor, the first and second images using the one or more registration parameters, and displaying, by a display output device, the registered first and second images. The respective first neutrosophic similarity scores for each of the first plurality of pixels provide a set of parameters, one parameter being the distance from the skin to the region of interest.

Another embodiment relates to a method for use with a medical imaging system and for segmenting an object contained in an image. The method for use with a medical imaging system and for segmenting an object contained in an image including receiving an image including a plurality of pixels at a processor from a scan, transforming, by the processor, a plurality of characteristics of each of the plurality of pixels into respective neutrosophic set domains, calculating, by the processor, a neutrosophic similarity score for each of the plurality of pixels based on the respective neutrosophic set domains for the characteristics of each of the plurality of the pixels, segmenting, by the processor, an object from a background of the image using a region growing algorithm based on the neutrosophic similarity score for the pixel, saving, by the processor, a distance from skin to the object to localize the object in a future scan, receiving a margin adjustment related to the object segmented from the background of the image at the processor, and displaying, by a display output device, the margin adjusted image. The neutrosophic similarity scores for each of the plurality of pixels provide a set of parameters, one parameter being the distance from the skin to the object.

The imaging device may use an imaging modality including at least one of ultrasound imaging, photoacoustic imaging, magnetic resonance imaging, computed tomography imaging, fluoroscopic imaging, x-ray imaging, fluorescence imaging and nuclear scan imaging.

The processing unit may further be configured to receive an annotation related to the region of interest segmented from the background of the first image, store the annotation related to the object segmented from the background of the first image; segment the region of interest from a background of the second image using the region growing algorithm based on the respective second neutrosophic similarity scores for each of the second plurality of pixels; and overlay the annotation relative to the region of interest segmented from the background of the second image.

The system may further include an augmented reality head-mounted device configured to: receive the second image with the overlaid annotation; display the second image with the overlaid annotation to a user; send information regarding the user's movement to the processing unit; and receive an adjusted second image from the processing unit based on at least one of a position or an orientation of the second image with the overlaid annotation.

The region of interest may include at least one of a lesion, a tumor, an organ, and a fiducial. The first image may be a pre-operative image and the second image is a real-time, intra-operative image, each providing at least one of a two-dimensional and a three-dimensional visualization of the region of interest.

A method for use with a medical imaging system and for registering a plurality of images containing an object includes: receiving a first image including a first plurality of pixels from a first scan at a processor; calculating, by the processor, respective first neutrosophic similarity scores for each of the first plurality of pixels of the first image; segmenting, by the processor, an object from a background of the first image using a region growing algorithm based on the respective first neutrosophic similarity scores for each of the first plurality of pixels, wherein the respective first neutrosophic similarity scores for each of the first plurality of pixels provide a set of parameters, one parameter being a distance from skin to the region of interest; receiving a margin adjustment related to the object segmented from the background of the first image at the processor; detecting, by the processor, the region of interest in a second scan based on the distance from the skin to the region of interest to localize the region of interest; receiving a second image including a second plurality of pixels from the second scan at the processor; calculating, by the processor, respective second neutrosophic similarity scores for each of the second plurality of pixels of the second image; performing, by the processor, a template matching algorithm based on differences between the respective first and second neutrosophic similarity scores for each of the first and second plurality of pixels of the first and second images, respectively, to determine one or more registration parameters; registering, by the processor, the first and second images using the one or more registration parameters; and displaying, by a display output device, the registered first and second images.

The one or more registration parameters may be determined by minimizing the differences between the respective first and second neutrosophic similarity scores for each of the first and second plurality of pixels of the first and second images, respectively. The method may include segmenting the object from background in the second image using the region growing algorithm based on the respective second neutrosophic similarity scores for each of the second plurality of pixels. The method may include receiving a margin adjustment related to the object segmented from the background of the second image. The method may include merging a pixel into a region containing the object under the condition that the respective first or second neutrosophic similarity score for the pixel is less than a threshold value. The method may include merging a pixel into a region containing the background under the condition that the respective first or second neutrosophic similarity score for the pixel is greater than a threshold value. Calculating the respective first or second neutrosophic similarity scores for each of the first and second plurality of pixels of the first or second image may further include: transforming a plurality of characteristics of each of the first and second plurality of pixels of the first or second image into respective neutrosophic set domains; and calculating the respective first or second neutrosophic similarity scores for each of the first and second plurality of pixels based on the respective neutrosophic set domains for the plurality of characteristics of each of the first and second plurality of pixels.

Calculating the respective first or second neutrosophic similarity scores for each of the first and second plurality of pixels based on the respective neutrosophic set domains for the plurality of characteristics of each of the first and second plurality of pixels may include: calculating respective first or second neutrosophic similarity scores for each of the respective neutrosophic set domains; and calculating a mean of the respective first or second neutrosophic similarity scores for each of the respective neutrosophic set domains. The plurality of characteristics may include at least one of a respective intensity, a respective textural value, a respective homogeneity, a pixel density, and dimensions of a region of interest. The respective intensity and homogeneity of each of the first and second plurality of pixels may be transformed into an intensity and homogeneity neutrosophic set domain based on a respective intensity and homogeneity value, respectively.

The method may further include receiving an annotation related to the object segmented from the background of the first image; storing the annotation related to the object segmented from the background of the first image; and overlaying the annotation relative to the object segmented from the background of the second image. The first image ma be a pre-operative image and the second image is a real-time, intra-operative image, each providing at least one of a 2D and 3D visualization of the object. The object may include at least one of a lesion, a tumor, an organ, tissue, and a fiducial.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

DETAILED DESCRIPTION

Referring to Figures generally, techniques for providing real-time visualization are described herein that are capable of importing a prior analysis of a specific data onto real-time images such as real-time, intra-operative images. A region growing algorithm for performing an image segmentation based on neutrosophic similarity scores is described. This region growing algorithm can be applied to extract an object (e.g., a lesion region of interest such as a tumor, organ or other tissue of interest) from a pre-operative image (e.g., the "first image" as also described herein). As used herein, a pre-operative image is scanned, and optionally analyzed, before a medical procedure. For example, the pre-operative image can be an image of a breast tumor. Following segmentation, a medical professional (e.g., a radiologist) can analyze and annotate the pre-operative image and/or the object extracted there from, and this analysis can be stored for subsequent use. During the surgery, a real-time, intra-operative image (e.g., the "second image" as also described herein) can be captured. A registration algorithm for registering the pre-operative image and the real-time, intra-operative based on neutrosophic similarity scores is described. According to the registration algorithm, the segmentation results in the pre-operative image can be used as reference. Following registration, the prior analysis, which is stored for subsequent use, can be overlaid (e.g., after being coordinated and adjusted) on the real-time, intra-operative image. Accordingly, the prior analysis can be imported onto or fused with the real-time, intra-operative medical image, which can be used by a medical professional (e.g., a surgeon) during the surgery for guidance. This allows the surgeon to see the real-time area of interest, without the need of importing static, less accurate images. In other words, this allows the surgeon to visualize the area of interest in real-time, which can improve surgical resections.

An example method for segmenting an object contained in an image includes receiving an image including a plurality of pixels, transforming a plurality of characteristics of a pixel into respective neutrosophic set domains, calculating a neutrosophic similarity score for the pixel based on the respective neutrosophic set domains for the characteristics of the pixel, segmenting an object from background of the image using a region growing algorithm based on the neutrosophic similarity score for the pixel, and receiving a margin adjustment related to the object segmented from the background of the image. The steps for segmenting can be performed using at least one processor. Optionally, the processor can be part of a cloud computing environment.

The image can provide a two-dimensional ("2D") or three-dimensional ("3D") visualization of the object, for example. Example imaging modalities that provide 2D or 3D visualizations include, but are not limited to, ultrasound imaging, photoacoustic imaging, magnetic resonance imaging ("MRI"), computed tomography ("CT") imaging, fluoroscopic imaging, x-ray imaging, fluorescence imaging and nuclear scan imaging. In addition, the object can be a lesion region of interest such as a tumor, organ or other tissue of interest, for example.

Additionally, the method can include receiving an annotation related to the object segmented from the background of the image. For example, a medical professional such as a radiologist can analyze the image and/or the object and provide the annotation (e.g., measurements, labels, notes, etc.) in order to highlight features (e.g., suspicious areas, blood vessels, vital structures, surrounding organs etc.) contained within the image and/or the object. It should be understood that the annotations can be used by another medical professional such as a surgeon, for example, as guidance during a subsequent medical procedure or consultation. Additionally, the method can further include storing the annotation related to the object segmented from the background of the image. As described below, the annotation related to the object segmented from the image can be overlaid on a real-time, image such as an intra-operative image.

Additionally, when using the region growing algorithm, the pixel can be merged into a region containing the object under the condition that the neutrosophic similarity score for the pixel is less than a threshold value, and the pixel can be merged into a region containing the background under the condition that the neutrosophic similarity score for the pixel is greater than a threshold value.

Alternatively or additionally, the plurality of characteristics can include an intensity of the pixel, a textural value of the pixel and/or a homogeneity of the pixel. Additionally, the step of calculating the neutrosophic similarity score for the pixel based on the respective neutrosophic set domains for the characteristics of the pixel can include calculating respective neutrosophic similarity scores for each of the respective neutrosophic set domains, and calculating a mean of the respective neutrosophic similarity scores for each of the respective neutrosophic set domains. In addition, the intensity of the pixel can be transformed into an intensity neutrosophic set domain based on an intensity value. Alternatively or additionally, the homogeneity of the pixel can be transformed into a homogeneity neutrosophic set domain based on a homogeneity value. The method can further include filtering the image to obtain the homogeneity of the pixel.

Alternatively or additionally, each of the respective neutrosophic set domains can include a true value, an indeterminate value and a false value.

An example method for registering a plurality of images containing an object can include receiving a first image including a plurality of pixels, calculating respective first neutrosophic similarity scores for each of the pixels of the first image, segmenting an object from background of the first image using a region growing algorithm based on the respective first neutrosophic similarity scores for each of the pixels, and receiving a margin adjustment related to the object segmented from the background of the image. The method can also include receiving a second image including a plurality of pixels, and calculating respective second neutrosophic similarity scores for each of the pixels of the second image. The method can further include performing a template matching algorithm based on differences between the respective first and second neutrosophic similarity scores for each of the pixels of the first and second images, respectively, to determine one or more registration parameters, and registering the first and second images using the one or more registration parameters. The steps for registering the plurality of images can be performed using at least one processor. Optionally, the processor can be part of a cloud computing environment.

The first and second images can provide a 2D or 3D visualization of the object, for example. Example imaging modalities that provide 2D or 3D visualizations include, but are not limited to, ultrasound imaging, photoacoustic imaging, MRI, CT imaging, fluoroscopic imaging, x-ray imaging, fluorescence imaging and nuclear scan imaging. In addition, the object can be a lesion region of interest such as a tumor, organ or other tissue of interest, for example.

Additionally, the registration parameters can be determined by minimizing the differences between the respective first and second neutrosophic similarity scores for each of the pixels of the first and second images, respectively.

Alternatively or additionally, the method can further include segmenting the object from background in the second image using the region growing algorithm based on the respective second neutrosophic similarity scores for each of the pixels. Alternatively or additionally, the method can further include receiving a margin adjustment related to the object segmented from the background of the second image.

Additionally, when using the region growing algorithm, the pixel can be merged into a region containing the object under the condition that the neutrosophic similarity score for the pixel is less than a threshold value, and the pixel can be merged into a region containing the background under the condition that the neutrosophic similarity score for the pixel is greater than a threshold value.

Alternatively or additionally, the step of calculating the respective first or second neutrosophic similarity scores for each of the pixels of the first or second image can include transforming a plurality of characteristics of each of the pixels of the first or second image into respective neutrosophic set domains, and calculating the respective first or second neutrosophic similarity scores for each of the pixels based on the respective neutrosophic set domains for the characteristics of each of the pixels.

Alternatively or additionally, the plurality of characteristics can include a respective intensity of each of the pixels, a respective textural value of each of the pixels and/or a respective homogeneity of each of the pixels. Additionally, the step of calculating the respective first or second neutrosophic similarity scores for each of the pixels based on respective neutrosophic set domains for the characteristics of each of the pixels can include calculating respective neutrosophic similarity scores for each of the respective neutrosophic set domains, and calculating a mean of the respective neutrosophic similarity scores for each of the respective neutrosophic set domains. In addition, the respective intensity of each of the pixels can be transformed into an intensity neutrosophic set domain based on a respective intensity value. Alternatively or additionally, the respective homogeneity of each of the pixels can be transformed into a homogeneity neutrosophic set domain based on a respective homogeneity value. The method can further include filtering the image to obtain the respective homogeneity of the pixel.

Alternatively or additionally, each of the respective neutrosophic set domains can include a true value, an indeterminate value and a false value.

Alternatively or additionally, the method can further include receiving an annotation related to the object segmented from the background of the first image. For example, a medical professional such as a radiologist can analyze the image and/or the object and provide the annotation (e.g., mark-ups, notes, etc.) in order to highlight features (e.g., blood vessels) contained within the first image and/or the object. It should be understood that the annotations can be used by another medical professional such as a surgeon, for example, as guidance during a subsequent medical procedure or consultation. Additionally, the method can further include storing the annotation related to the object segmented from the background of the image. Optionally, the method can further include overlaying the annotation relative to the object segmented from the background of the second image.

Alternatively or additionally, the method can further include transmitting the second image with the overlaid annotation to an augmented reality ("AR") head-mounted device, and displaying the second image with the overlaid annotation on the AR head-mounted device. Optionally, the method can further include receiving information regarding a user's movement from the AR head-mounted device, adjusting a position and/or an orientation of the second image with the overlaid annotation, and transmitting the adjusted second image with the overlaid annotation to the AR head-mounted device, for example, for display on the AR head-mounted device.

Additionally, the first image can be a pre-operative image. The pre-operative image can be the image that is analyzed by the medical professional (e.g., a radiologist) and annotated as described above. In addition, the second image can be a real-time, intra-operative image. The real-time, intra-operative image can have the annotation from the pre-operative image overlaid thereon, which can aid the other medical professional (e.g., a surgeon) during a subsequent medical procedure or consultation.

It should be understood that the above-described subject matter may also be implemented as a computer-controlled apparatus, a computing system, or an article of manufacture, such as a computer-readable storage medium.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. While implementations will be described for performing image segmentation and registration algorithms on medical images (e.g., ultrasound images) based on neutrosophic similarity scores, it will become evident to those skilled in the art that the implementations are not limited thereto, but are applicable for performing image segmentation and registration algorithms on other types of images including, but not limited to, photoacoustic images, MRIs, CT images, fluoroscopic images, x-ray images, fluorescence images and nuclear scan images. It will also become evident that the segmentation and registration algorithms are applicable to fields other than medicine.

Figure 1:
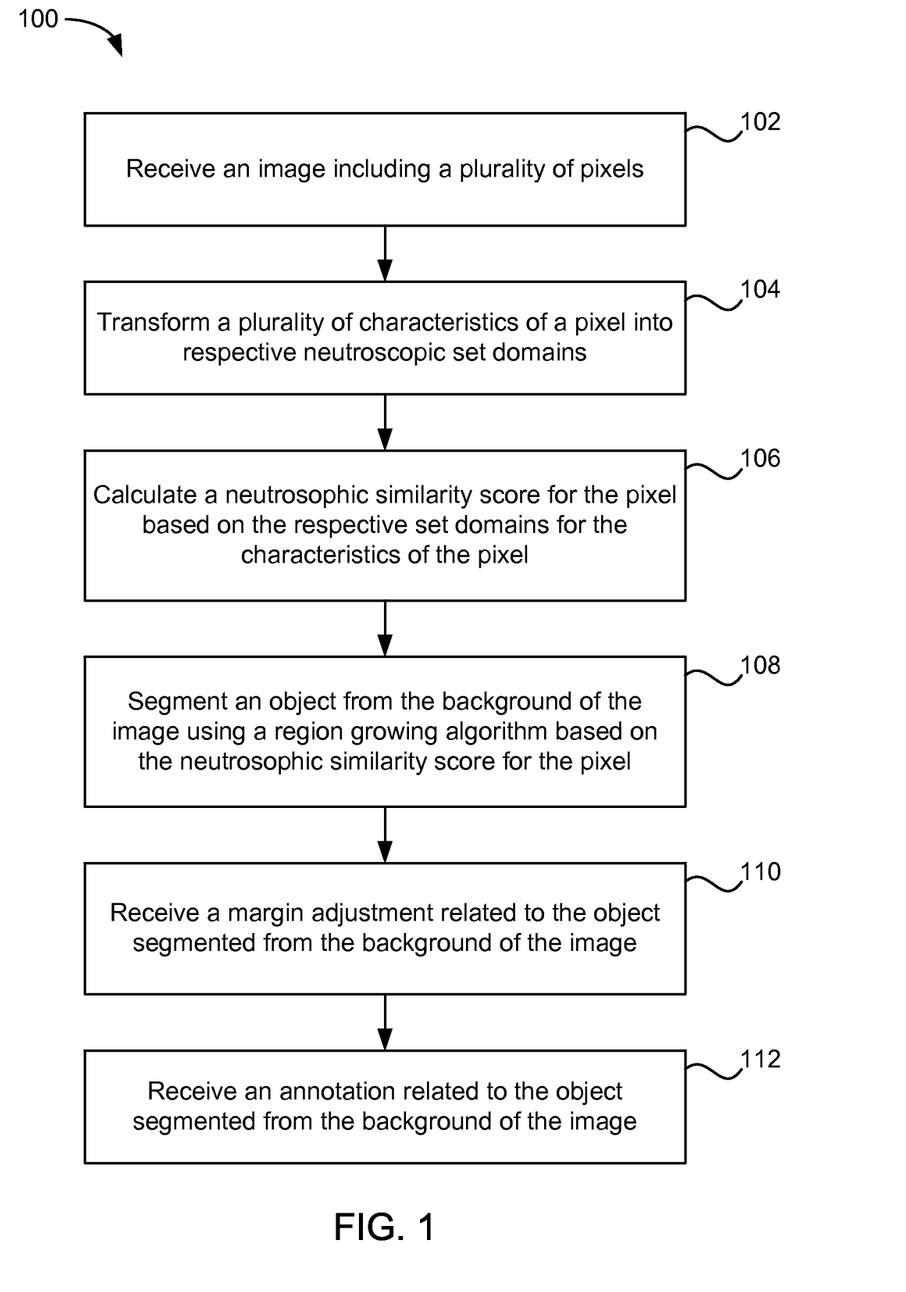
FIG. 1 is a flow diagram illustrating example operations for performing a region growing algorithm based on neutrosophic similarity scores according to an example embodiment.
Figure 2:
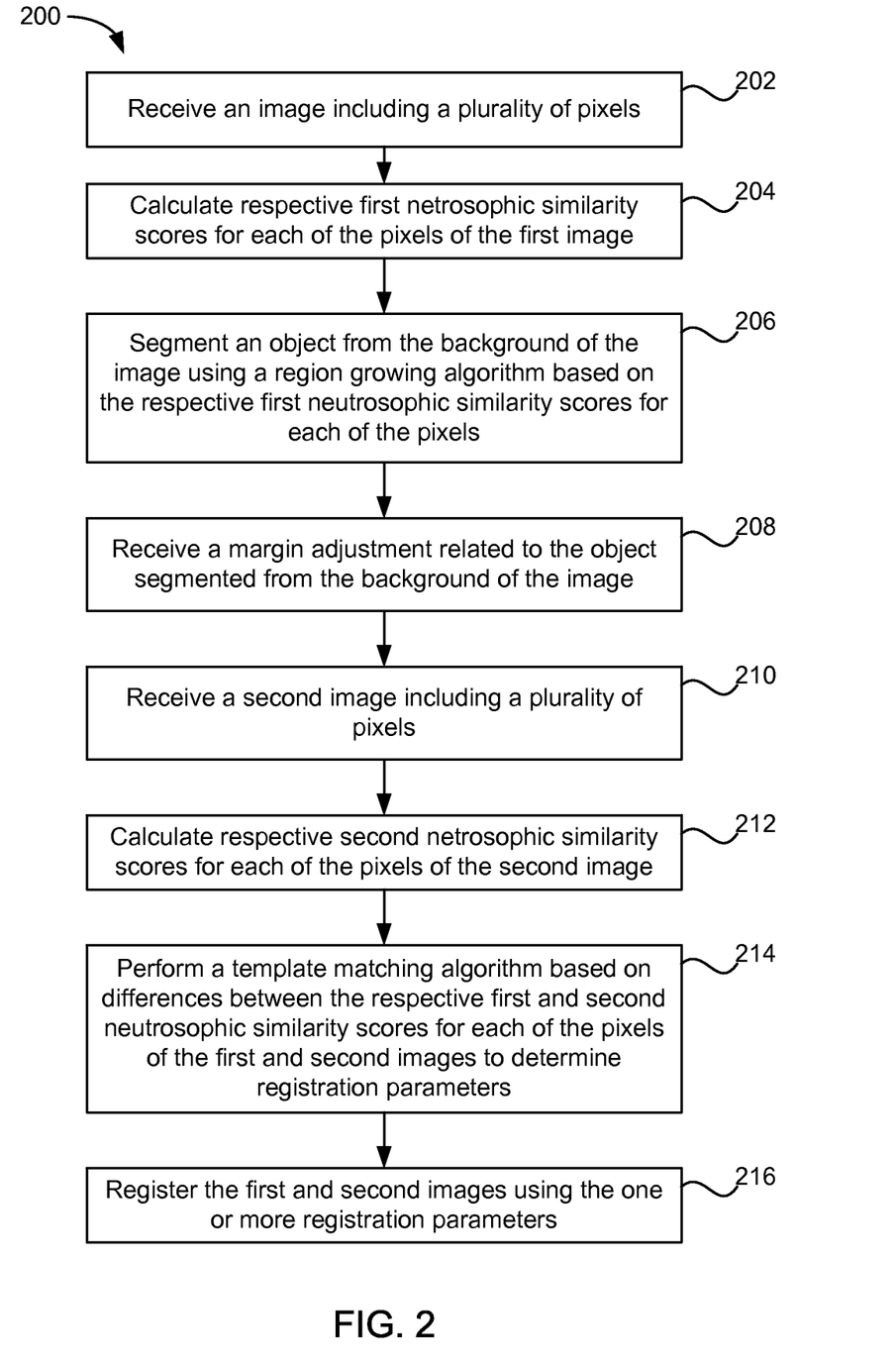
FIG. 2 is a flow diagram illustrating example operations for performing image registration based on neutrosophic similarity scores according to an example embodiment.

Referring now to FIGS. 1 and 2, example image segmentation and registration techniques are described. It should be understood that the image segmentation and registration techniques can be performed by at least one processor (described below). Additionally, the image segmentation and registration techniques can optionally be implemented within a cloud computing environment, for example, in order to decrease the time needed to perform the algorithms, which can facilitate visualization of the prior analysis on real-time images. Cloud computing is well-known in the art. Cloud computing enables network access to a shared pool of configurable computing resources (e.g., networks, servers, storage, applications, and services) that can be provisioned and released with minimal interaction. It promotes high availability, on-demand self-services, broad network access, resource pooling and rapid elasticity. It should be appreciated that the logical operations described herein with respect to the various figures may be implemented (1) as a sequence of computer implemented acts or program modules (i.e., software) running on a computing device, (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Referring now to FIG. 1, a flow diagram illustrating example operations 100 for performing a region growing algorithm based on neutrosophic similarity scores is shown. At 102, an image including a plurality of pixels is received. The image can provide a 2D or 3D visualization of an object, for example. Example imaging modalities that provide 2D or 3D visualizations include, but are not limited to, ultrasound imaging, photoacoustic imaging, MRI, CT imaging, fluoroscopic imaging, x-ray imaging, fluorescence imaging and nuclear scan imaging. In the examples provided below, the image is a 3D ultrasound image, for example, acquired with by the iU22 xMATRIX ULTRASOUND SYSTEM from KONINKLIJKE PHILIPS N.V. of EINDHOVEN, THE NETHERLANDS. 3D ultrasound systems are portable, relatively inexpensive, and do not subject a patient to ionizing radiation, which provide advantages over CT scans (radiation exposure) and MRIs (relatively large system) for real-time image guidance. However, as described above, this disclosure contemplates using images acquired by any imaging modality that provides a 2D or 3D visualization. Additionally, the object can be a lesion region of interest such as a tumor, organ or other tissue of interest, for example. In the examples provided below, the image is an image of breast tissue of a subject and the object is a tumor. However, as described above, this disclosure contemplates using images of other tissue and objects other than tumors. The subject or patient described herein can be human and non-human mammals of any age.

At 104, a plurality of characteristics of a pixel are transformed into respective neutrosophic set domains. Each of the respective neutrosophic set domains can include a true value, an indeterminate value and a false value. Additionally, the plurality of characteristics can include, but are not limited to, an intensity value of the pixel, a textural value of the pixel and/or a homogeneity value of the pixel. In other words, this disclosure contemplates transforming pixel characteristics other than intensity, texture and homogeneity into neutrosophic set domains. In the examples described below, an intensity image and a homogeneity image are transformed into respective neutrosophic set domains. Although the examples involve transforming two pixel characteristics into respective neutrosophic set domains and calculating a neutrosophic similarity score there from, this disclosure contemplates transforming more or less than two pixel characteristics (e.g., one, three, four, etc. pixel characteristics) into respective neutrosophic set domains and calculating a neutrosophic similarity score there from.

The intensity image can be defined using intensity values for the pixels and transformed into the neutrosophic set domain as shown by Eqns. (1)-(5).

$$T_{In}(x, y) = \frac{g(x, y) - g_{min}}{g_{max} - g_{min}} \quad (1)$$

$$I_{In}(x, y) = \frac{\delta(x, y) - \delta_{min}}{\delta_{max} - \delta_{min}} \quad (2)$$

$$\delta(x, y) = |g(x, y) - \bar{g}(x, y)| \quad (3)$$

$$\bar{g}(x, y) = \frac{1}{w \times w} \sum_{m=x-w/2}^{x+w/2} \sum_{n=j-w/2}^{y+w/2} g(m, n) \quad (4)$$

$$F_{In}(x, y) = 1 - T(x, y) \quad (5)$$

where $\bar{g}(x, y)$ is the local mean value, and $\delta(x, y)$ is the absolute value of the difference between intensity $g(x, y)$ and its local mean value at $(x, y)$, and $x$ and $y$ are pixel coordinates in the intensity image.

The homogeneity image can be defined using texture values for the pixels and transformed into neutrosophic set domain as shown by Eqns. (6)-(9). To obtain the homogeneity image (e.g., homogeneity values for each of the pixels), the image can be filtered, for example, using a texture energy measurement ("TEM") filter, mean filter, Gaussian filter, median filter, etc.

$$T_{Ho}(x, y) = \frac{H(x, y) - H_{min}}{H_{max} - H_{min}} \quad (6)$$

$$I_{Ho}(x, y) = 1 - \frac{Gd_k(x, y) - Gd_{kmin}}{Gd_{kmax} - Gd_{kmin}} \quad (7)$$

$$F_{Ho}(x, y) = 1 - T_{Ho}(x, y) \quad (8)$$

$$H(x, y) = TEM(g(x, y)) \quad (9)$$

where H(x, y) is the homogeneity value at (x, y), which is depicted as the filtering result with the TEM filters. $Gd_k$(x, y) is the gradient magnitude on H(x, y), x and y are pixel coordinates in the homogeneity image.

At 106, a neutrosophic similarity score for the pixel can be calculated based on the respective neutrosophic set domains for the characteristics of the pixel. For example, respective neutrosophic similarity scores for each of the respective neutrosophic set domains (e.g., the neutrosophic set domains for the intensity values and the homogeneity values) can be calculated as shown by Eqns. (10)-(11). The neutrosophic similarity score for the intensity image ($NS_{In}$(x, y)) is shown by Eqn. (10), and the neutrosophic similarity score for the homogeneity image ($NS_{Ho}$(x, y)) is shown by Eqn. (11).

$$NS_{In}(x, y) = \frac{T_{In}(x, y)}{\sqrt{T_{In}^2(x, y) + I_{In}^2(x, y) + F_{In}^2(x, y)}} \quad (10)$$

$$NS_{Ho}(x, y) = \frac{T_{Ho}(x, y)}{\sqrt{T_{Ho}^2(x, y) + I_{Ho}^2(x, y) + F_{Ho}^2(x, y)}} \quad (11)$$

Then, a mean of the respective neutrosophic similarity scores for each of the respective neutrosophic set domains (e.g., the neutrosophic set domains for the intensity values and the homogeneity values) can be calculated as shown by Eqn. (12). As described above, a mean of any number of neutrosophic similarity scores (e.g., one for each pixel characteristic transformed into the neutrosophic set domain) can be calculated.

$$NS = \frac{NS_{In} + NS_{Ho}}{2} \quad (12)$$

At 108, an object or region of interest (ROI) (e.g., a lesion region of interest such as a tumor, organ or other tissue of interest) can be segmented from background of the image using a region growing algorithm based on the neutrosophic similarity score for the pixel. For example, an initial region or seed points can be selected on the image, and neighboring pixels (e.g., pixels neighboring or adjacent to the initial region or seed points) can grow into the object region according their respective neutrosophic similarity score differences ($Dif_{NS}$), which is shown by Eqn. (13). If the difference is less than a threshold value, a pixel can be merged into the object region. If the difference is greater than the threshold value, a pixel can be merged into the background region. This step (e.g., step 108) is iteratively performed until no pixels satisfies the criterion.

$$Dif_{NS} = NS(x, y) - \overline{Obj}_{NS} \quad (13)$$

where NS(x, y) is the neutrosophic similarity score at pixel, $\overline{Obj}_{NS}$ is a neutrosophic similarity score for the object region and x and y are pixel coordinates.

At 110, a margin adjustment related to the object segmented from the background of the image can be received. The margin adjustment is an adjustment to the margins or boundaries around the object segmented from the background of the image. For example, a medical professional (e.g., a radiologist) can review the segmented image, and based on his knowledge and experience, manually refine (e.g., expand or contract) the margins or boundaries of the object segmented using the region growing algorithm. This disclosure contemplates that the segmented object can be displayed in a 2D or 3D rendering with or without performing the margin adjustment. Optionally, the segmented object can be displayed using an AR head-mounted device (described below).

Optionally, at 112, an annotation related to the object segmented from the background of the image can be received. For example, a medical professional (e.g., a radiologist) can analyze the segmented image and/or the object and provide the annotation (e.g., mark-ups, notes, etc.) in order to highlight features (e.g., suspicious areas, blood vessels, etc.) contained within the image and/or the object. It should be understood that the annotations can be used by another medical professional such as a surgeon, for example, as guidance during a subsequent medical procedure or consultation. The annotation is also referred to herein as the "prior analysis." The annotation related to the object segmented from the background of the image can be stored, for example, for subsequent use by overlaying and displaying the annotation relative to a real-time, intra-operative image (described below). This disclosure contemplates that the segmented object and/or the annotation can be displayed in a 2D or 3D rendering with or without performing the margin adjustment. Optionally, the segmented object and/or the annotation can be displayed using an AR head-mounted device (described below).

Referring now to FIG. 2, a flow diagram illustrating example operations for performing image registration based on neutrosophic similarity scores is shown. At 202, a first image including a plurality of pixels is received. Similar as above, the first image may provide a 2D or 3D visualization of the object, for example. Optionally, the first image may be a pre-operative image providing a 2D or 3D visualization of the object. The first image can be segmented and optionally analyzed to provide guidance to a medical professional (e.g., a surgeon) during a medical procedure (e.g., surgery). Accordingly, the first image can also be referred to as the "analyzed image." Additionally, the object (e.g., region of interest, etc.) can be a lesion region of interest such as a tumor, organ or other tissue of interest, for example. In the examples provided below, the image is an image of breast tissue of a subject and the object is a tumor.

At 204, respective first neutrosophic similarity scores for each of the pixels of the first image can be calculated. Neutrosophic similarity scores for the pixels of the first image can be calculated as described above. For example, a single pixel characteristic can be transformed into the neutrosophic set domain. Optionally, a plurality of pixel characteristics can be transformed into the neutrosophic set domain. The neutrosophic set domain can include a true value, an indeterminate value and a false value. Transforming a pixel characteristic into the neutrosophic set domain is shown by Eqns. (1)-(5) for intensity values and Eqns. (6)-(9) for homogeneity values. The pixel characteristics can include, but are not limited to, an intensity of the pixel, a textural value of the pixel and/or a homogeneity of the pixel. Additionally, neutrosophic similarity scores can be calculated, for example, as shown by Eqn. (10) for intensity values and Eqn. (11) for homogeneity values. Optionally, when neutrosophic scores for a plurality of pixel characteristics are calculated, a mean of the neutrosophic similarity scores can be calculated as shown by Eqn. (12).

At 206, an object can be segmented from background of the first image using a region growing algorithm based on the respective first neutrosophic similarity scores for each of the pixels. As described above, an initial region or seed points can be selected on the first image, and neighboring pixels (e.g., pixels neighboring or adjacent to the initial region or seed points) can grow into the object region according their respective neutrosophic similarity score differences ($Dif_{NS}$), which is shown by Eqn. (13). If the difference is less than a threshold value, a pixel can be merged into the object region. If the difference is greater than the threshold value, a pixel can be merged into the background region. This step (e.g., step 206) is iteratively performed until no pixels satisfies the criterion. At 208, a margin adjustment related to the object segmented from the background of the image can be received. As described above, the margin adjustment is an adjustment to the margins or boundaries around the object segmented from the background of the first image. For example, a medical professional (e.g., a radiologist) can review the segmented image, and based on his knowledge and experience, manually refine (e.g., expand or contract) the margins or boundaries of the object segmented using the region growing algorithm.

At 210, a second image including a plurality of pixels can be received. Similar as above, the second image can provide a 2D or 3D visualization of the object, for example. Optionally, the second image can be a real-time, intra-operative image providing a 2D or 3D visualization of the object. The second image can optionally be acquired with a 3D ultrasound system, which is portable, relatively inexpensive, and does not subject a patient to ionizing radiation, and therefore, makes it desirable for use in image guided surgery. Additionally, the object can be a lesion region of interest such as a tumor, organ or other tissue of interest, for example. In the examples provided below, the image is an image of breast tissue of a subject and the object is a tumor. The object in the second image (e.g., the real-time, intra-operative image) can be the same object (e.g., the same breast tumor) as the object in the first image (e.g., the pre-operative image).

At 212, respective second neutrosophic similarity scores for each of the pixels of the second image can be calculated. Neutrosophic similarity scores for the pixels of the second image can be calculated as described above. For example, a single pixel characteristic can be transformed into the neutrosophic set domain. Optionally, a plurality of pixel characteristics can be transformed into the neutrosophic set domain. The neutrosophic set domain can include a true value, an indeterminate value and a false value. Transforming a pixel characteristic into the neutrosophic set domain is shown by Eqns. (1)-(5) for intensity values and Eqns. (6)-(9) for homogeneity values. The pixel characteristics can include, but are not limited to, an intensity of the pixel, a textural value of the pixel and/or a homogeneity of the pixel. Additionally, neutrosophic similarity scores can be calculated, for example, as shown by Eqn. (10) for intensity values and Eqn. (11) for homogeneity values. Optionally, when neutrosophic scores for a plurality of pixel characteristics are calculated, a mean of the neutrosophic similarity scores can be calculated as shown by Eqn. (12). The respective second neutrosophic similarity scores for each of the pixels of the second image (e.g., the real-time, intra-operative image) can be based on the same pixel characteristic(s) as the respective first neutrosophic similarity scores for each of the pixels of the first image (e.g., the pre-operative image).

At 214, a template matching algorithm can be performed based on differences between the respective first and second neutrosophic similarity scores for each of the pixels of the first and second images, respectively, to determine one or more registration parameters. The registration parameters can be determined by minimizing the differences between the respective first and second neutrosophic similarity scores for each of the pixels of the first and second images, respectively. For example, the object region in the first image segmentation results can be used as a template (e.g., a 3D template, etc.). After calculating the respective neutrosophic similarity scores for each of the pixels of the second image (e.g., step 212), a rotation on the template (e.g., the 3D template, etc.) can be taken and the neutrosophic score difference of the object region of the second image can be computed, which is shown in Eqn. (14).

$$Dif_{NS}(x_o, y_o, z_o, \phi) = \sum_{x=1}^{H}\sum_{y=1}^{W}\sum_{z=1}^{L} |NS_2(x+x_o, y+y_o, z+z_o) - NS_1(x, y, z)| \qquad (14)$$

where $NS_1$ is the respective neutrosophic similarity scores for each of the pixels of the first image, $NS_2$ is the respective neutrosophic similarity scores for each of the pixels of the second image, and x, y and z are pixel coordinates in 3D space. A loop can then be taken on $x_o$, $y_o$, $z_o$, and $\phi$ in the range of [1 $H_2$], [1 $W_2$], [1 $Z_2$], and [−10 10], respectively, where $H_2$, $W_2$ and $Z_2$ are the height, width and length of the second image. The optimal $x_o$, $y_o$, $z_o$, and $\phi$ can be obtained with the lowest $Dif_{NS}$. Then, at 216, the first and second images can be registered using the one or more registration parameters. For example, the template (e.g., the 3D template, etc.) can be transformed using the optimal $x_o$, $y_o$, $z_o$, and $\phi$ as the registration parameters, and the transformed result can be used as the object region within the second image.

Optionally, in order to refine the object region of the second image as determined through the registration algorithm described above, the object in the second image can be segmented from background using the region growing algorithm described above with regard to FIG. 1. Optionally, this segmentation can include receiving a margin adjustment related to the object segmented from the background of the second image. The margin adjustment is an adjustment to the margins or boundaries around the object segmented from the background of the second image. For example, a medical professional (e.g., a radiologist, etc.) can review the segmented image, and based on his knowledge and experience, manually refine (e.g., expand or contract) the margins or boundaries of the object segmented using the region growing algorithm.

Alternatively or additionally, after segmenting the first image (e.g., the pre-operative image) using the region growing algorithm at step 206, an annotation related to the object segmented from the background of the first image can be received. For example, a medical professional (e.g., a radiologist, etc.) can analyze the segmented image and/or the object and provide the annotation (e.g., mark-ups, notes, etc.) in order to highlight features (e.g., suspicious areas, blood vessels, etc.) contained within the first image and/or the object. It should be understood that the annotations can be used by another medical professional such as a surgeon, for example, as guidance during a subsequent medical procedure or consultation. The annotation related to the object segmented from the background of the first image can be stored, for example, for subsequent use by overlaying and displaying the annotation relative to the second image (e.g., the real-time, intra-operative image, etc.). This disclosure contemplates that the segmented object and/or the annotation can be displayed in a 2D or 3D rendering with or without performing the margin adjustment. Optionally, the segmented object and/or the annotation can be displayed using an AR head-mounted device (described below).

Figure 3:
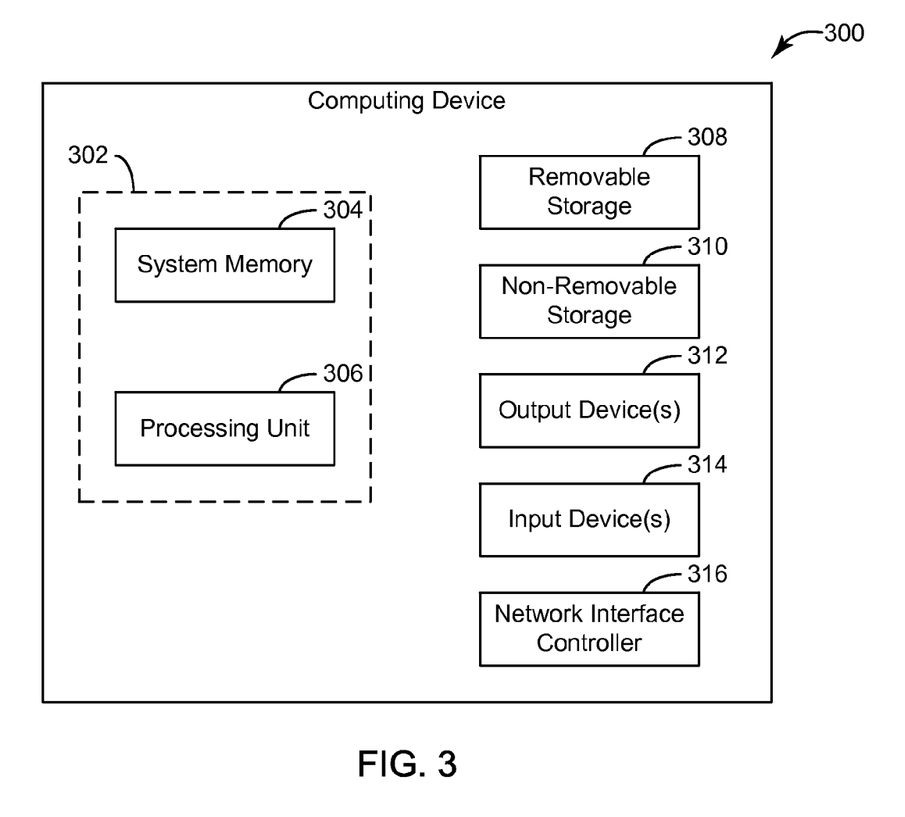
FIG. 3 is a block diagram of a computing device according to an example embodiment.

When the logical operations described herein are implemented in software, the process may execute on any type of computing architecture or platform. For example, referring to FIG. 3, an example computing device upon which embodiments of the invention may be implemented is illustrated. In particular, at least one processing device described above may be a computing device, such as computing device 300 shown in FIG. 3. The computing device 300 may include a bus or other communication mechanism for communicating information among various components of the computing device 300. In its most basic configuration, computing device 300 typically includes at least one processing unit 306 and system memory 304. Depending on the exact configuration and type of computing device, system memory 304 may be volatile (such as random access memory (RAM)), non-volatile (such as read-only memory (ROM), flash memory, etc.), or some combination of the two. This most basic configuration is illustrated in FIG. 3 by dashed line 302. The processing unit 306 may be a standard programmable processor that performs arithmetic and logic operations necessary for operation of the computing device 300.

Computing device 300 may have additional features/functionality. For example, computing device 300 may include additional storage such as removable storage 308 and non-removable storage 310 including, but not limited to, magnetic or optical disks or tapes. Computing device 300 may also contain network connection(s) 316 that allow the device to communicate with other devices. Computing device 300 may also have input device(s) 314 such as a keyboard, mouse, touch screen, etc. Output device(s) 312 such as a display, speakers, printer, etc. may also be included. The additional devices may be connected to the bus in order to facilitate communication of data among the components of the computing device 300. All these devices are well known in the art and need not be discussed at length here.

The processing unit 306 may be configured to execute program code encoded in tangible, computer-readable media. Computer-readable media refers to any media that is capable of providing data that causes the computing device 300 (i.e., a machine) to operate in a particular fashion. Various computer-readable media may be utilized to provide instructions to the processing unit 306 for execution. Common forms of computer-readable media include, for example, magnetic media, optical media, physical media, memory chips or cartridges, a carrier wave, or any other medium from which a computer can read. Example computer-readable media may include, but is not limited to, volatile media, non-volatile media and transmission media. Volatile and non-volatile media may be implemented in any method or technology for storage of information such as computer readable instructions, data structures, program modules or other data and common forms are discussed in detail below. Transmission media may include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 306 may execute program code stored in the system memory 304. For example, the bus may carry data to the system memory 304, from which the processing unit 306 receives and executes instructions. The data received by the system memory 304 may optionally be stored on the removable storage 308 or the non-removable storage 310 before or after execution by the processing unit 306.

Computing device 300 typically includes a variety of computer-readable media. Computer-readable media can be any available media that can be accessed by device 300 and includes both volatile and non-volatile media, removable and non-removable media. Computer storage media include volatile and non-volatile, and removable and non-removable media implemented in any method or technology for storage of information such as computer readable instructions, data structures, program modules or other data. System memory 304, removable storage 308, and non-removable storage 310 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 300. Any such computer storage media may be part of computing device 300.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Figure 4:
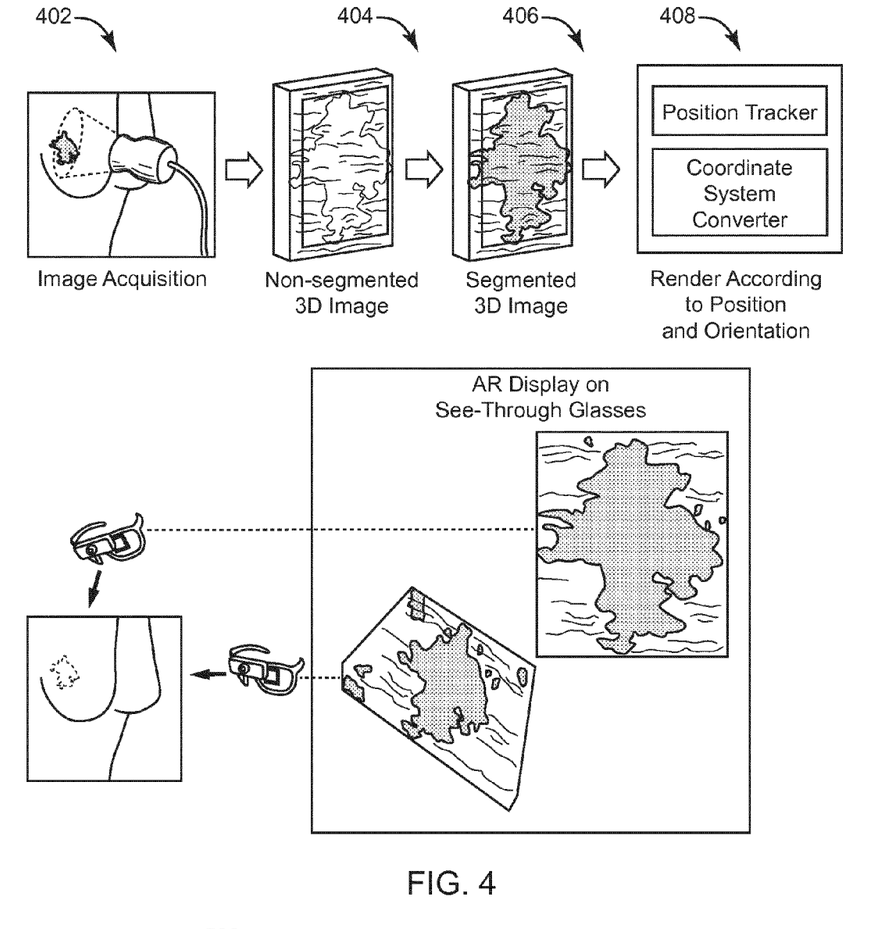
FIG. 4 is a flow diagram of example operations for providing real-time visualization of a prior image analysis on real-time images according to an example embodiment.

FIG. 4 is a flow diagram of example operations for providing real-time visualization of a prior image analysis on real-time images. The example operations were used to evaluate 3D ultrasound images and confirm accuracy for real-time volumetric analysis. The example operations include performing the segmentation and registration algorithms described with regard to FIGS. 1 and 2. For example, at 402, a pre-operative image is acquired. The pre-operative image provides a 3D visualization of an object (e.g., a tumor within breast tissue). As described above, the tumor can be segmented from the background of the pre-operative image using the region growing algorithm based on neutrosophic similarity scores. A medical professional (e.g., a radiologist) then marks suspicious areas for later resection, i.e., the radiologist provides the annotations described above. Thereafter, a real-time, intra-operative ultrasound image is acquired, for example, using the iU22 xMATRIX ULTRASOUND SYSTEM from KONINKLIJKE PHILIPS N.V. of EINDHOVEN, THE NETHERLANDS. The real-time, intra-operative ultrasound image provides a 3D visualization of the tumor within breast tissue. As described above, the pre-operative image and the real-time, intra-operative ultrasound image are registered using a registration algorithm based on neutrosophic similarity scores. By registering the pre-operative image and the real-time, intra-operative ultrasound image, the annotation made to the pre-operative image (e.g., the prior analysis) can be imported and overlaid on (or fused with) the real-time, intra-operative image, which is shown at 404. This allows for real-time visualization of the tumor with the radiologist's annotation. The precision of the image segmentation and registration algorithms described herein are confirmed in by the feasibility study results of Table 1, showing an accuracy of less than 1.5 mm deviation per axis. These results demonstrate the accuracy and reliability of real-time, 3D visualization.

TABLE 1

| Accuracy of Algorithms (n = 27) | | | |
|---|---|---|---|
| Axis | x (mm) | y (mm) | z (mm) |
| Accuracy | 1.44 | 1.61 | 0.85 |
| SD | 1.66 | 1.5 | 0.89 |
| SEM | 0.43 | 0.39 | 0.23 |

Figure 5:
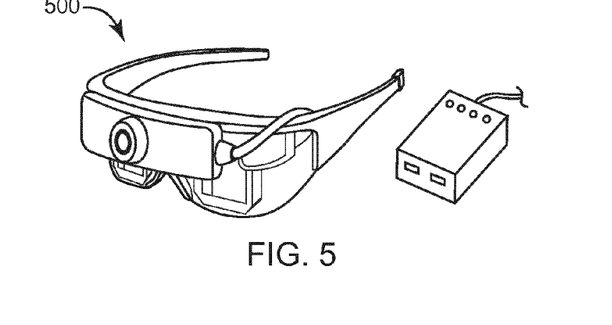
FIG. 5 is an example AR head-mounted device used in the example operations shown in FIG. 4.

The enhanced images (e.g., the real-time, intra-operative ultrasound image with annotations overlaid) can be displayed, and optionally, in a 3D modality. For example, the image segmentation and registration algorithms described above can be integrated with head-tracking (HT) and AR technologies (e.g., the "AR head-mounted device 500" as used herein). One example AR head-mounted device 500 is the VUZIX STAR 1200XLD from VUZIX CORPORATION of ROCHESTER, NEW YORK, which is shown in FIG. 5. Although the VUZIX STAR 1200XLD is provided as an example, this disclosure contemplates integrating the image segmentation and registration algorithms with other AR head-mounted devices. This can provide surgeons with an accurate, real-time, 3D navigation tool for intra-operative guidance, facilitating complete tumor excision. For example, at 406, the real-time, intra-operative ultrasound image with the overlaid annotation can be transmitted to the AR head-mounted device 500. The computing device 300 that performs the image segmentation and/or registration algorithms can be communicatively connected with the AR head-mounted device 500 through a communication link. This disclosure contemplates the communication link is any suitable communication link. For example, a communication link may be implemented by any medium that facilitates data exchange between the network elements including, but not limited to, wired, wireless and optical links. The real-time, intra-operative ultrasound image with the overlaid annotation can then be displayed on the AR head-mounted device 500.

The HT technology of the AR head-mounted device 500 allows the computing device 300 that performs the image segmentation and/or registration algorithms to detect the position and orientation of a user's (e.g., the surgeon's) head to display the image as an AR figure. For example, at 408, information regarding a user's movement can be received at the computing device 300 from the AR head-mounted device 500, and the computing device 300 can adjust a position and/or an orientation of the real-time, intra-operative ultrasound image with the overlaid annotation. The adjusted real-time, intra-operative ultrasound image with the overlaid annotation can then be transmitted to the AR head-mounted device 500 by the computing device 300, for example, for display on the AR head-mounted device 500. Accordingly, in addition to the potential "x-ray vision" (e.g., seeing the tumor underneath the skin) capability, the AR head-mounted device 500 has a see-through display, allowing the surgeon to operate simultaneously in a traditional manner.

Figure 6:
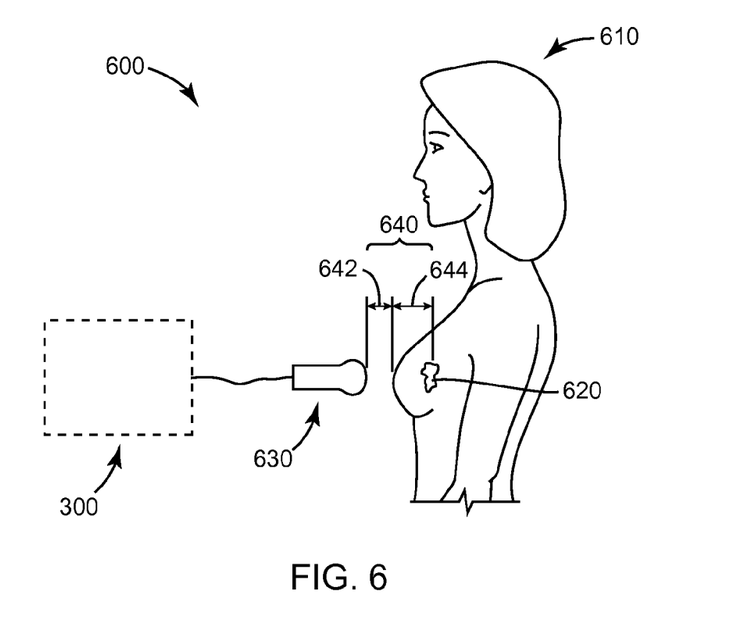
FIG. 6 is an illustration of acquiring an image of a region of interest according to an example embodiment.
Figure 7:
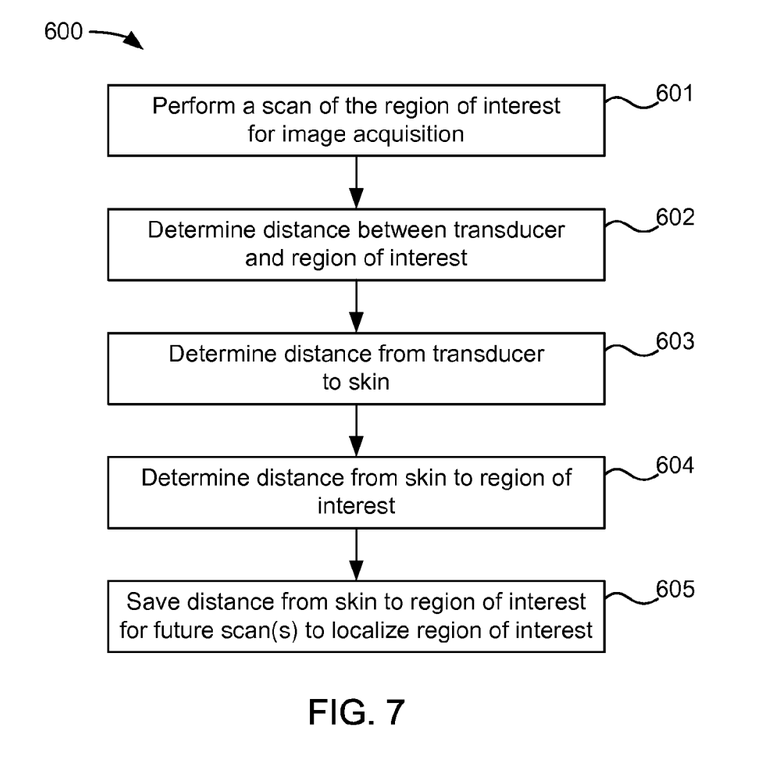
FIG. 7 is a flow diagram of determining a neutrosophic similarity score parameter for the region of interest of FIG. 6 according to an example embodiment.

Referring now to FIGS. 6 and 7, an additional parameter may be provided by the neutrosophic similarity scores that are specific to a particular finding in a imaging study (e.g., via imaging modalities that provide 2D or 3D visualizations including ultrasound imaging, photoacoustic imaging, MRI, CT imaging, fluoroscopic imaging, x-ray imaging, fluorescence imaging, nuclear scan imaging, etc.). As mentioned above, the set of parameters provided by the neutrosophic scores can include, but are not limited to, pixel characteristics such as an intensity of the pixel, a textural value of the pixel, a homogeneity of the pixel, pixel density, as well as the specific dimensions (e.g., area, volume, width, length, height, etc.) of the object or region of interest (ROI). The ROI may be a lesion region of interest such as a tumor, an organ, or other structures such as a fiducial or other area of interest. An additional parameter provided by the neutrosophic similarity scores may be the distance from the skin of a patient or subject (e.g., human, non-human mammals, etc.) to the ROI (e.g., tumor, organ, another structure, etc.). This parameter (e.g., the distance from the skin to the ROI, etc.) tends to be substantially stable throughout various evaluations (e.g., from a first scan to a second scan, over time, etc.). Also, the parameter of distance from the skin to the ROI adds increased specificity of the finding(s) (e.g., tumor, etc.).

As shown in FIGS. 6-7, a method 600 of determining a distance from the skin of a subject (e.g., patient, etc.) to a region of interest is shown according to an example embodiment. In one example embodiment, method 600 may be implemented with the computing device 300 of FIG. 3. Accordingly, method 600 may be described in regard to FIG. 3. Also, method 600 may be used to supplement the method 100 of FIG. 1 and/or the method 200 of FIG. 2. Accordingly, method 600 may be described in regard to FIGS. 1-2.

As shown in FIGS. 6-7, the method 600 is shown to be a pre-operative scan of a subject, shown as female patient 610, to examine a region of interest, shown as tumor 620, within the breast tissue of the female patient 610. As mentioned above, this disclosure contemplates scanning other tissue and regions of interest other than tumors (e.g., organs, etc.) of humans (e.g., male, female, etc.) and non-human mammals of any age (e.g., adult, adolescent, etc.). At 601, image acquisition is received from the scan (e.g., first scan, pre-operative scan, etc.) performed on the region of interest. For example, the computing device 300 may include a communication mechanism (e.g., a bus communication system, wireless communication, wired communication, etc.) for communicating information among various components of the computing device 300. The computing device 300 may also have input device(s) 314, including a transducer 630. In the example embodiment, the transducer 630 is an ultrasound transducer. In other embodiments, the transducer 630 may be structure as another type of transducer (e.g., used in imaging modalities that provide 2D or 3D visualizations including photoacoustic imaging, MRI, CT imaging, fluoroscopic imaging, x-ray imaging, fluorescence imaging, nuclear scan imaging, etc.). Transducer 630 is configured to send signals (e.g., sound waves, etc.) to the ROI (e.g., tumor 620, etc.) and receive reflected signals (e.g., echoes of the sent sound waves, etc.) back. Via this method, transducer 630 may transmit the data (e.g., via a bus or other communication mechanism), in the form of an image of the tumor 620 or other ROI, to the system memory 304 of the computing device 300 (e.g., step 102 of method 100, step 202 of method 200, etc.).

At 602, a distance between the transducer 630 and the tumor 620, shown as transducer-to-ROI distance 640, is determined. The transducer-to-ROI distance 640 includes two sub-distances, shown as transducer-to-skin distance 642 and skin-to-ROI distance 644. As mentioned above, the computing device 300 may execute program code stored in the system memory 304. For example, the communication mechanism may carry the data acquired by the transducer 630 to the system memory 304, from which the processing unit 306 receives and executes instructions. The data received by the system memory 304 may optionally be stored on the removable storage 308 or the non-removable storage 310 before or after execution by the processing unit 306. The transducer-to-ROI distance 640 may be determined by processing unit 306 from an elapsed time for a sound wave to be sent and return to the transducer 630 from the tumor 620. For example, the elapsed time is used to determine the transducer-to-ROI distance 640 by assuming that speed of sound is constant. Thereby, with the elapsed time and speed, processing unit 306 may determine the transducer-to-ROI distance 640 and store it in at least one of system memory 304, removable storage 308, and non-removable storage 310.

At 603, a distance between the transducer 630 and the skin (e.g., breast, etc.) of the subject (e.g., female patient 610, etc.), shown as transducer-to-skin distance 642, is determined. The transducer-to-skin distance 642 is determined in a substantially similar manner to the transducer-to-ROI distance 640. For example, the elapsed time of the sounds waves returning to the transducer may vary in time based on which surface each reflects off of. Therefore, the elapsed time of the sound waves used to determine the transducer-to-ROI distance 640 are substantially longer than the elapsed time of the sound waves used to determine the transducer-to-skin distance 642. Thereby, the processing unit 306 may segment the data received from the transducer 630 based on the substantial differentiation between the times. With the elapsed time (e.g., time for sound waves to reflect of the skin and return to transducer 630, substantially shorter time, etc.) and the speed (e.g., speed of sound, etc.), processing unit 306 may determine the transducer-to-skin distance 642 and store it in at least one of system memory 304, removable storage 308, and non-removable storage 310. In some embodiments, the transducer-to-skin distance 642 may be negligible or substantially negligible, as the transducer 630 may be in direct contact with the skin of the subject. In other embodiments, the distance between two objects (e.g., the transducer 630 and the skin, the transducer 630 and the ROI, the skin and the ROI, etc.) may be measured using a different medium (e.g., not an elapsed time, etc.).

At 604, a distance from the skin to the ROI is determined. For example, the skin-to-ROI distance 644 may be determined by the processing unit 306 from the transducer-to-ROI distance 640 and the transducer-to-skin distance 642 stored in the memory of computing device 300 (e.g., system memory 304, removable storage 308, non-removable storage 310, etc.). As shown in FIG. 6, the skin-to-ROI distance 644 is the difference between the transducer-to-ROI distance 640 and the transducer-to-skin distance 642. In some embodiments, the transducer-to-ROI distance 640 and the skin-to-ROI distance 644 may be substantially equivalent (e.g., when the transducer 630 is in direct contact with the skin, when the transducer-to-skin distance 642 is negligible, etc.). At 605, the skin-to-ROI distance 644 is saved to the memory of the computing device 300. In some embodiments, the skin-to-ROI distance 644 may be saved with various other parameters determined by the neutrosophic similarity scores (e.g., as described in step 106 of method 100, step 204 of method 200, etc.). The skin-to-ROI distance 644 may be used as parameter to localize the region of interest. For example, the skin-to-ROI distance 644 may be used to supplement future scans (e.g., a second scan, an intra-operative scan, etc.). Such as detecting the region of interest (e.g., tumor 620, organ, other structure, etc.) in a second scan based on the distance from the skin to the region of interest to localize the region of interest. Following the localization of the ROI, steps 210-216 of method 200 may be implemented.

In other embodiments, the distance from the skin to the ROI may be determined using a different imaging modality. As mentioned above, the transducer 630 may be may be structure as another type of transducer (e.g., used in imaging modalities that provide 2D or 3D visualizations including photoacoustic imaging, MRI, CT imaging, fluoroscopic imaging, x-ray imaging, fluorescence imaging, nuclear scan imaging, etc.). Thereby, the skin-to-ROI distance 644 (i.e., the transducer-to-ROI distance 640, the transducer-to-skin distance 642, etc.) may be determined and saved to the memory of a computing device of any of the above mentioned imaging modalities (e.g., photoacoustic imaging, MRI, CT imaging, fluoroscopic imaging, x-ray imaging, fluorescence imaging, nuclear scan imaging, etc.).

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. In a medical imaging system having an imaging device configured to scan a region of interest to acquire at least one of (i) a primary image including a first plurality of pixels during a first scan and (ii) a secondary image including a second plurality of pixels during a second, subsequent scan and a processing unit communicably and operatively coupled to the imaging device, the processing unit configured to receive the primary image from the first scan, transform a plurality of characteristics of each of the first plurality of pixels into respective first neutrosophic set domains, calculate respective first neutrosophic similarity scores for each of the first plurality of pixels of the primary image based on parameters in the respective first neutrosophic set domains, and segment the region of interest from a background of the primary image using a region growing algorithm based on the respective first neutrosophic similarity scores for each of the first plurality of pixels, the processing unit further configured to:

utilize the respective first neutrosophic similarity scores for each of the first plurality of pixels to provide a set of parameters, one parameter being a distance from skin to the region of interest, to localize a position of the region of interest in the secondary image; and detect the region of interest in the second, subsequent scan based on the respective first neutrosophic set domains acquired from the first scan, including the distance from the skin to the region of interest obtained from the primary image to localize and segment the region of interest for further processing.

2. The processing unit of claim 1, wherein the set of parameters of the respective first neutrosophic similarity scores are selected by an operator of the medical imaging system to be segmented in the secondary image.

3. The processing unit of claim 1, that the processing unit is configured to:

calculate respective second neutrosophic similarity scores for each of the second plurality of pixels of the secondary image;

segment the region of interest in the secondary image based on the set of parameters of the respective first neutrosophic similarity scores and the respective second neutrosophic similarity scores; and facilitate displaying the region of interest in the secondary image.

4. The processing unit of claim 1, wherein the set of parameters of the respective first neutrosophic similarity scores include at least one of pixel intensity, pixel gradient, pixel homogeneity, a position of structures of the region of interest, a shape of the structures of the region of interest, a volume of the structures of the region of interest, a distance between the structures of the region of interest, and an orientation of the structures of the region of interest.

5. The processing unit of claim 1, wherein the primary image is a pre-operative image.

6. The processing unit of claim 5, wherein the secondary image is an intra-operative image.

7. The processing unit of claim 1, wherein the secondary image is at least one of a pre-operative image and a post-operative image.

8. The processing unit of claim 1, wherein the second, subsequent scan includes a plurality of second, subsequent scans to acquire a plurality of second images associated with the primary image.

9. The processing unit of claim 1, wherein the processing unit is configured to:

determine a first distance from the imaging device and the region of interest;

determine a second distance from the imaging device to the skin; and determine a third distance from the skin to the region of interest based on the difference between the first distance and the second distance.

10. The processing unit of claim 9, wherein the processing unit is configured to determine the first distance based on a first elapsed time for a signal to be sent by and return to the imaging device, and wherein the processing unit is configured to determine the second distance based on a second elapsed time for the signal to be sent by and return to the imaging device.

11. The processing unit of claim 10, wherein the third distance is further based on the difference between the first elapsed time and the second elapsed time.

12. The processing unit of claim 10, wherein the imaging device is an ultrasound imaging device and the signal is a sound wave.

* * * * *

UNITED STATES PATENT AND TRADEMARK OFFICE
CERTIFICATE OF CORRECTION

PATENT NO. : 9,443,161 B2
APPLICATION NO. : 14/518976
DATED : September 13, 2016
INVENTOR(S) : Yanhui Guo It is certified that error appears in the above-identified patent and that said Letters Patent is hereby corrected as shown below:

On the Title Page

Item (72) should read "Inventors: Yanhui Guo, Miami, FL (US); Segundo J. Gonzalez, Tampa, FL (US)"

Signed and Sealed this
Thirtieth Day of April, 2019

Andrei Iancu
*Director of the United States Patent and Trademark Office*